(12) United States Patent
Halstead et al.

(10) Patent No.: US 7,351,386 B2
(45) Date of Patent: Apr. 1, 2008

(54) CARTRIDGE HOLDER FOR AUTOMATED REPROCESSOR

(75) Inventors: Eric Halstead, Beauport (CA); Serge Coulombe, Boischatel (CA)

(73) Assignee: Steris Inc, Temecula, CA (US)

( * ) Notice: Subject to any disclaimer, the term of this patent is extended or adjusted under 35 U.S.C. 154(b) by 1000 days.

(21) Appl. No.: 10/116,393

(22) Filed: Apr. 4, 2002

(65) Prior Publication Data

US 2003/0190257 A1   Oct. 9, 2003

(51) Int. Cl.
   *A61L 2/18* (2006.01)
(52) U.S. Cl. .................. 422/261; 422/28; 422/255; 422/276; 422/292
(58) Field of Classification Search .................. 422/28, 422/292, 255, 261, 276; 222/464.2, 485, 222/464.4, 465
   See application file for complete search history.

(56) References Cited

U.S. PATENT DOCUMENTS

| | | | |
|---|---|---|---|
| 4,429,423 A * | 2/1984 | Syrenne | 4/225.1 |
| 4,731,222 A | 3/1988 | Kralovic et al. | |
| 4,943,414 A | 7/1990 | Jacobs et al. | |
| 5,037,623 A | 8/1991 | Schneider et al. | |
| 5,209,909 A | 5/1993 | Siegel et al. | |
| 5,217,698 A | 6/1993 | Siegel et al. | |
| 5,225,160 A | 7/1993 | Sanford et al. | |
| 5,279,799 A | 1/1994 | Moser | |
| 5,494,530 A | 2/1996 | Graf | |
| 5,494,637 A | 2/1996 | Barlow | |
| 5,551,462 A | 9/1996 | Biermaier | |
| 5,552,115 A | 9/1996 | Malchesky | |
| 5,580,530 A | 12/1996 | Kowatsch et al. | |
| 5,641,464 A | 6/1997 | Briggs, III et al. | |
| 5,662,866 A | 9/1997 | Siegel et al. | 422/29 |

(Continued)

FOREIGN PATENT DOCUMENTS

WO   WO 01/56614   8/2001

OTHER PUBLICATIONS

Dictionary definition for "fitting", www.webster.com.*

(Continued)

*Primary Examiner*—Gladys J P Corcoran
*Assistant Examiner*—Sean E. Conley
(74) *Attorney, Agent, or Firm*—Fay Sharpe LLP

(57) ABSTRACT

A cartridge holder (30) for an automated endoscope reprocessor (10) is mounted on a movable rack (14). As the rack is wheeled into the chamber, a connector (164) on the cartridge holder (164) automatically makes a fluid connection with a connection port (158) within the chamber. The cartridge holder includes a base (42) and a lid (44), which is pivotally connected to the base by a hinge (110). A cartridge (40) holding a dose of a disinfectant concentrate or reagents is positioned in a well (50) defined by the base and the lid closed. Water flows through the cartridge holder via a fluid passageway (A) defined in part by the lid and in part by the hinge. The water mixes with the concentrate or reagents and the resulting disinfectant solution passes out of a lower end (205) of the cartridge into the well. The solution flows upwardly, around the cartridge, through an annular space (232) between the cartridge and the well, disinfecting the well in the process. The solution exits the cartridge through a plurality of bores (80) at an upper end of the base.

27 Claims, 8 Drawing Sheets

U.S. PATENT DOCUMENTS

| | | | |
|---|---|---|---|
| 5,711,921 A | 1/1998 | Langford | |
| 5,749,385 A | 5/1998 | Rochette et al. | |
| 5,753,195 A | 5/1998 | Langford et al. | |
| 5,840,251 A | 11/1998 | Iwaki | |
| 5,906,802 A | 5/1999 | Langford | |
| 5,988,050 A * | 11/1999 | Foster, Jr. | 99/467 |
| 5,992,673 A * | 11/1999 | Hwang | 220/819 |
| 5,997,814 A | 12/1999 | Minerovic et al. | |
| 6,013,227 A | 1/2000 | Lin et al. | |
| 6,015,529 A | 1/2000 | Lin et al. | |
| 6,027,572 A | 2/2000 | Labib et al. | |
| 6,039,724 A | 3/2000 | Seifert et al. | 604/533 |
| 6,066,294 A | 5/2000 | Lin et al. | |
| 6,068,815 A | 5/2000 | Oberleitner et al. | |
| 6,120,729 A | 9/2000 | Schad | |
| 6,264,902 B1 | 7/2001 | Howlett | |
| 6,325,968 B1 | 12/2001 | Fricker et al. | |
| 6,364,103 B1 | 4/2002 | Sergio et al. | 206/222 |
| 6,482,358 B1 * | 11/2002 | Kelsch et al. | 422/28 |
| 2001/0016176 A1 | 8/2001 | Lin et al. | |
| 2001/0031221 A1 | 10/2001 | Wu et al. | |
| 2001/0033805 A1 | 10/2001 | Jacobs et al. | |
| 2001/0033807 A1 | 10/2001 | Lin et al. | |
| 2001/0036422 A1 | 11/2001 | Lin et al. | |

OTHER PUBLICATIONS

"Chemical-Thermal Disinfection", INNOVA 2000 reliable automatic disinfection of endoscopes. BHT-INNOVA 2000.

* cited by examiner

CARTRIDGE HOLDER FOR AUTOMATED REPROCESSOR

BACKGROUND OF THE INVENTION

The present invention relates to the field of disinfection or sterilization of medical, pharmaceutical, dental, or mortuary devices, and the like. It finds particular application in conjunction with a cartridge holder for a disinfectant or sterilant concentrate for use in the cleaning and disinfecting of flexible endoscopes, and will be described with particular reference thereto. It should be appreciated, however, that the invention is also applicable to the treatment of other devices.

Fluid microbial decontamination systems are typically designed to cause microbes on the item to be removed or killed by a fluid anti-microbial agent. This is achieved in a variety of ways, including bath of anti-microbial liquid, spraying the item with anti-microbial liquid, surrounding the item with anti-microbial vapor, and the like.

Liquid microbial decontamination systems are now widely used for equipment which could not withstand the high temperatures of steam sterilization. Commonly, a technician mixes a liquid disinfectant or sterilant composition, such as peracetic acid or other strong oxidant, and manually immerses the items to be microbially decontaminated in the composition. The high degree of manual labor introduces numerous uncontrolled and unreported variables into the process. There are quality assurance problems with technician errors in the mixing of sterilants, control of immersion times, rinsing of residue, exposure to the ambient atmosphere after the rinsing step, and the like.

To deliver reproducible amounts of sterilants to the microbial decontamination system, a number of packaging systems have been developed. One problem to overcome is that cleaning agents, such as detergents, and pretreatment agents, such as buffers and corrosion inhibitors, tend to degrade peracetic acid. Combining them with liquid peracetic acid results in a reduced shelf life. Thus, for peracetic sterilants, in particular, such components of a treatment system are generally kept separate to prolong shelf life. U.S. Pat. No. 5,037,623 to Schneider, et al., for example, discloses a cup which contains a measured dose of a liquid peracetic acid concentrate. Buffers, detergents, and anticorrosive agents, in the form of a powder, are separately contained. The cup includes a linear vent passage which extends into the interior of the cup. A gas permeable membrane is mounted over the interior end of the vent passage to allow venting of the container during storage.

U.S. Pat. No. 5,662,866 to Siegel, et al. discloses a two-compartment cup for powdered sterilant reagent components. An outer compartment holds a first reagent while an inner compartment, disposed within the outer compartment, holds a second reagent. The two reagents react in water to form an oxidant, such as peracetic acid. Pretreatment agents, such as surfactants, corrosion inhibitors, and sequestering agents, are often included in one of the two compartments. Peripheral walls of inner and outer cups are affixed together at flanges adjacent their open ends to define the two compartments. A permeable sheet is affixed to the inner cup flange for ventedly sealing both cups. The outer cup is closed at its base by a first detachable base and the inner cup is similarly closed by a second detachable base.

To release the sterilant into the fluid flow path of a microbial decontamination system, the cup is inserted into a well in fluid communication with the system. In the case of the liquid sterilant cup, a peel-off top is removed to provide access to the contents of the cup. Alternatively, a cutter, such as that disclosed in U.S. Pat. No. 5,439,654 to Kochte, pierces the base of the cup with a blade. In the case of the powdered sterilant cup with a removable base, pressure is applied to detach the bases of the inner and outer cup portions. Minerovic, et al., U.S. Pat. Nos. 5,997,814 and 6,325,968, discloses two compartment cups in which parts of the cup are formed from a permeable material, allowing the contents of the cup to pass through when dissolved in water. A jet stream of water is sprayed into the cup to dissolve and flush the sterilizing agents from the cup.

In general, the water enters the top of the well, flows through the cup, and passes out of the well though an opening in the bottom. The walls of the well adjacent the sides of the cup, receive reduced contact with the sterilant or disinfectant. In cases where the devices being sterilized or disinfected are heavily contaminated with blood and other biological materials, biofilm may build up on the walls of the well. The biofilm could support microbes during periods of non-use. Rinse water passing through the well may occasionally pick up a portion of this biofilm, leading to recontamination of the devices.

The present invention provides for a new and improved cartridge holder for holding a multi-compartment cup, which overcomes the above-referenced problems and others.

SUMMARY OF THE INVENTION

In accordance with one aspect of the present invention, a decontamination system is provided. The system includes a chamber for receiving an item to be decontaminated. A cartridge holder is mounted within the chamber, which receives a single use cartridge containing a concentrated decontaminant or reagents which mix with water to form a decontaminant solution. The cartridge holder includes a base, which defines a well having an opening through which the cartridge is inserted into the well. A lid selectively closes the well opening. A plurality of bores adjacent an upper end of the well fluidly communicate between the well and the chamber, such that water entering the well is directed first through the cartridge before exiting the well through the bores. A fluid distribution system is fluidly connected with the cartridge holder for supplying the water to the well.

In accordance with another aspect of the present invention, a cartridge holder is provided. The cartridge holder includes a base, which defines a well for receiving a cartridge having a sidewall. The base has an opening adjacent an upper end thereof. The base includes a plurality of bores, which extend from the well to an exterior surface of the base adjacent the opening. A lid selectively closes the opening. A fluid passageway is at least partially defined by the lid and is fluidly connected with the well.

In accordance with another aspect of the present invention, a method of disinfection is provided. The method includes placing a cartridge in a well defined by a base through an opening in the well. The cartridge has a sidewall and upper and lower ends which selectively hold within the cartridge a disinfectant concentrate or reagents which react in a liquid to form a disinfectant solution. The method further includes closing the opening in the well with a lid and supplying the liquid to the well. The liquid is flowed into the cartridge through the upper end such that the liquid mixes with the concentrate or reagents to form the disinfectant solution. The disinfectant solution is flowed out of the cartridge into the well through the lower end of the cartridge. The disinfectant solution is flowed through a space between the cartridge sidewall and the well to disinfect the well. The disinfectant solution is flowed out of the well through a plurality of bores in the base adjacent an upper end of the well. Items to be disinfected are contacted with the disinfectant solution.

One advantage of at least one embodiment of the present invention is that sterilizing or disinfecting fluid is circulated over all surfaces of a cartridge holder, assuring that the cartridge holder is microbially decontaminated.

Another advantage of at least one embodiment of the present invention is that an operator is able to establish whether a cartridge has been used without opening the cartridge holder.

Another advantage of at least one embodiment of the present invention is that the cartridge holder acts as a manifold for gaseous and liquid passages, reducing the number of fluid connections which are to be made by an operator.

Another advantage resides in improved dissolving of powdered reagents.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
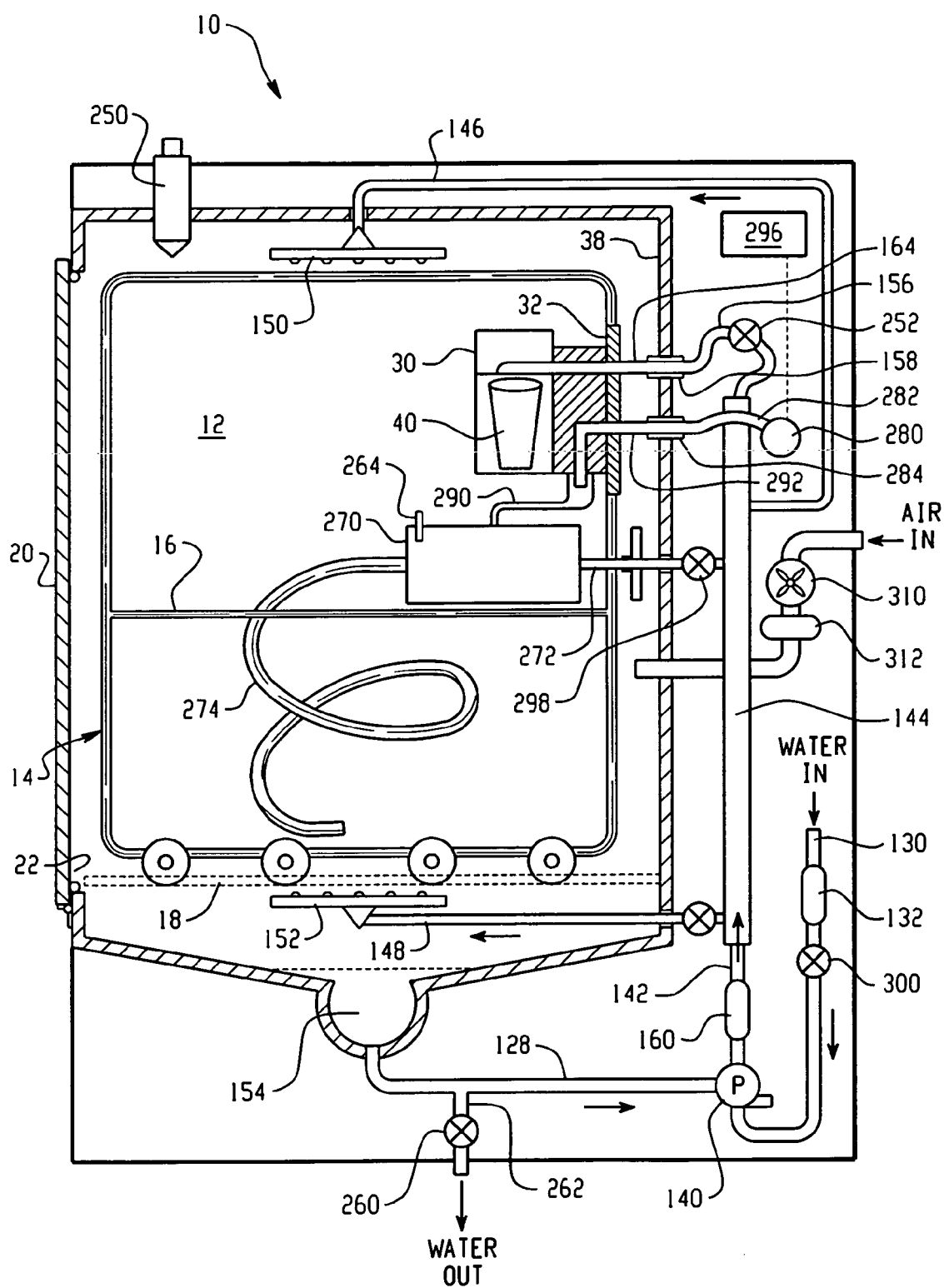
FIG. 1 is a side sectional view of an automated reprocessor according to the present invention.

With reference to FIG. 1, an automated reprocessor 10 defines an interior chamber 12, which receives a wheeled cart or rack 14. Items to be disinfected or otherwise decontaminated, such as endoscopes or other medical, dental, pharmaceutical or mortuary devices, and the like, are positioned in open baskets or shelves 16 of the cart 14. The cart 14 wheels into or out of the interior chamber 12 along tracks 18, positioned one adjacent each side of the chamber. A door 20 selectively closes an access opening 22 to the chamber. The reprocessor chamber 12 is preferably 10-15 liters in interior volume, allowing the reprocessor to be sized to fit under counters or other work surfaces. However, higher installation locations and other sized processors are also contemplated.

While the reprocessor 10 is described herein with particular reference to disinfecting and rinsing steps, it is also contemplated that additional steps are employed, such as a precleaning step. Additionally, while disinfection, which refers to the destruction or inactivation of all harmful microorganisms, is generally desired, it is also contemplated that higher levels of antimicrobial treatment are achieved, such as sterilization (the destruction or inactivation of all microorganisms, whether harmful or not), or lower levels, such as sanitization. The various levels of microbial decontamination can be achieved by adjusting the selected chemical agent, concentration of the chemical agent, cycle time, and the like.

Figure 2:
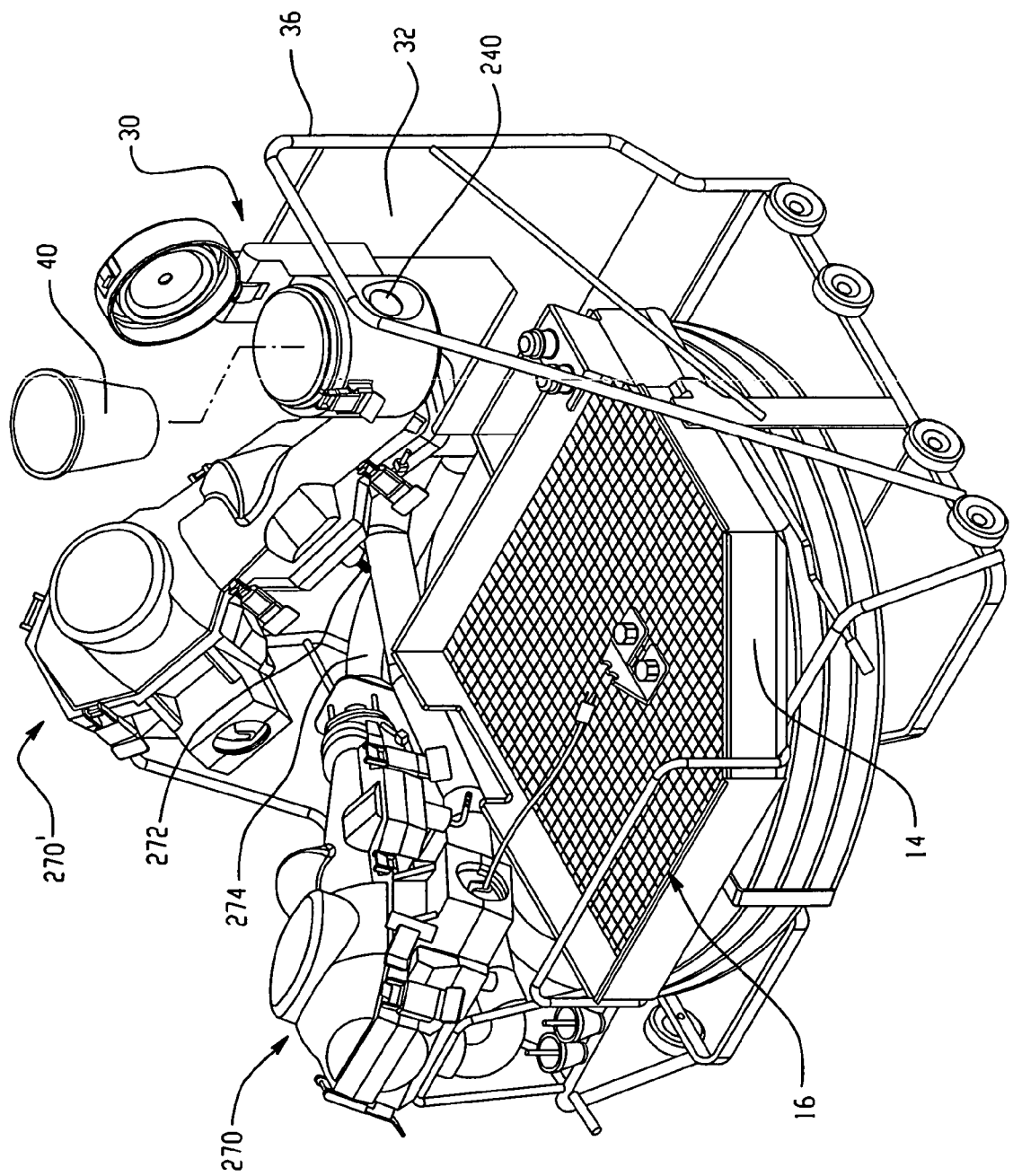
FIG. 2 is a perspective view of a rack of the reprocessor of FIG. 1 supporting a cartridge holder and two endoscope head containers according to the present invention.
Figure 3:
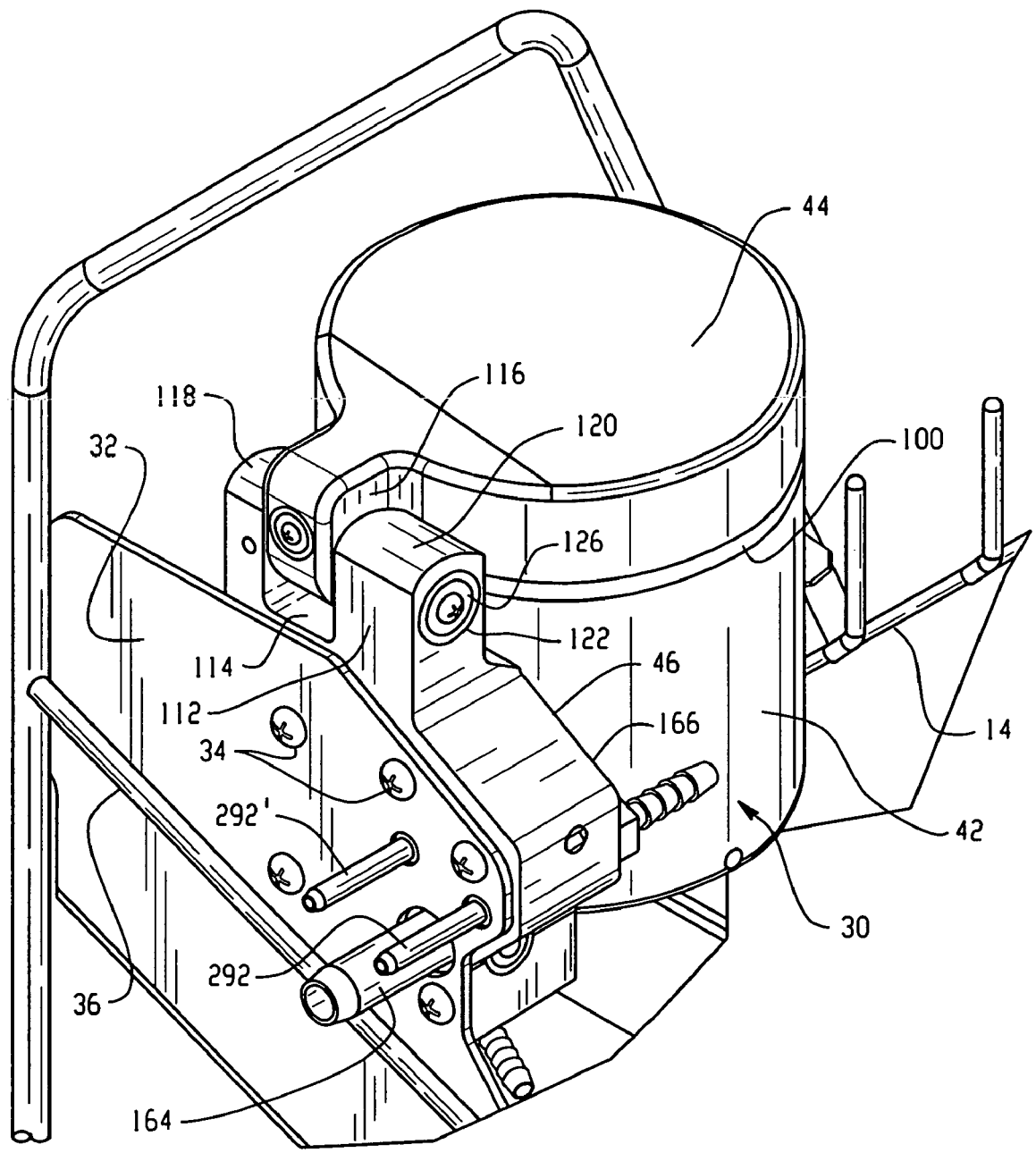
FIG. 3 is a rear perspective view of a rack of the reprocessor of FIG. 1 supporting a cartridge holder according to the present invention.
Figure 4:
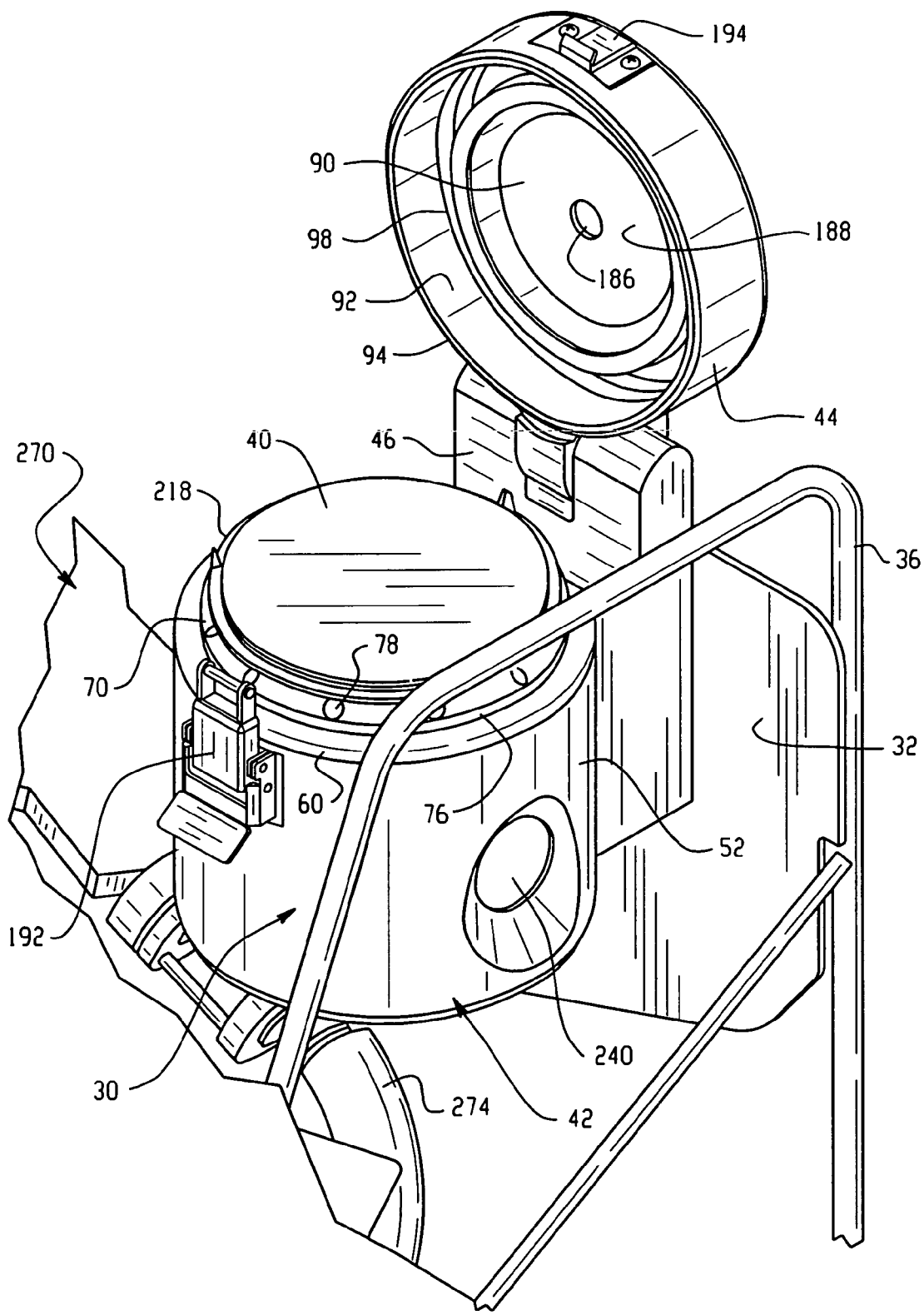
FIG. 4 is an enlarged perspective view of the cartridge holder of FIG. 1, with its lid opened to reveal a cartridge.

With reference also to FIGS. 2-4, a cartridge holder 30 is mounted on the illustrated cart 14 by a mounting bracket 32, using screws, bolts, or other fixing members 34. In a preferred embodiment, the mounting bracket 32 is attached to an upper rear portion 36 of the cart 14 such that it faces a rear wall 38 of the chamber 12 (FIG. 1).

Figure 5:
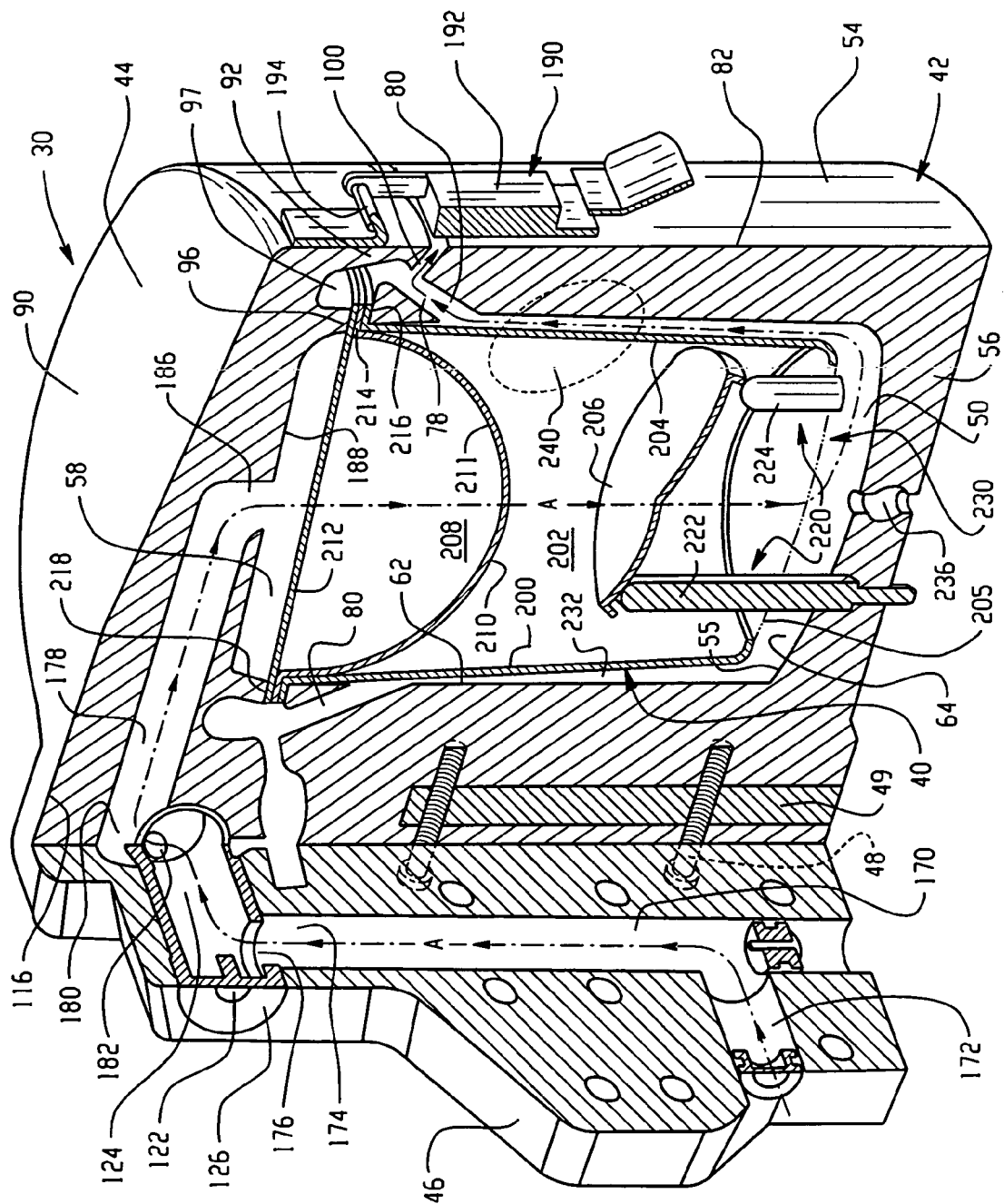
FIG. 5 is an enlarged perspective view, in partial section, of the cartridge holder of FIG. 1.

The cartridge holder 30 receives a cartridge or cup 40, which in the preferred embodiment, holds a measured dose of a concentrated source of a decontaminant, such as a disinfectant or sterilant. The source may be in liquid or solid form and is sealed within the cartridge 40 until use. The cartridge holder 30 includes a base 42, a lid 44, and a mounting member 46, through which the screws 34 are attached to the cartridge holder. The mounting member 46 is mounted to the base 42 by screws 48, or other suitable fixing members (FIG. 5). The lid 44, base 42, and mounting member 46 are advantageously formed from a rigid plastic, for example by molding, with inserts 49, formed from metal or other hard material which is capable of being tapped for receiving the screw threads.

While the cartridge holder 30 is advantageously mounted to the cart 14 for ease of access to and replacement of the cartridge 40, it is also contemplated that the cartridge holder be mounted elsewhere within the chamber 12, for example, to a wall of the chamber.

Figure 6:
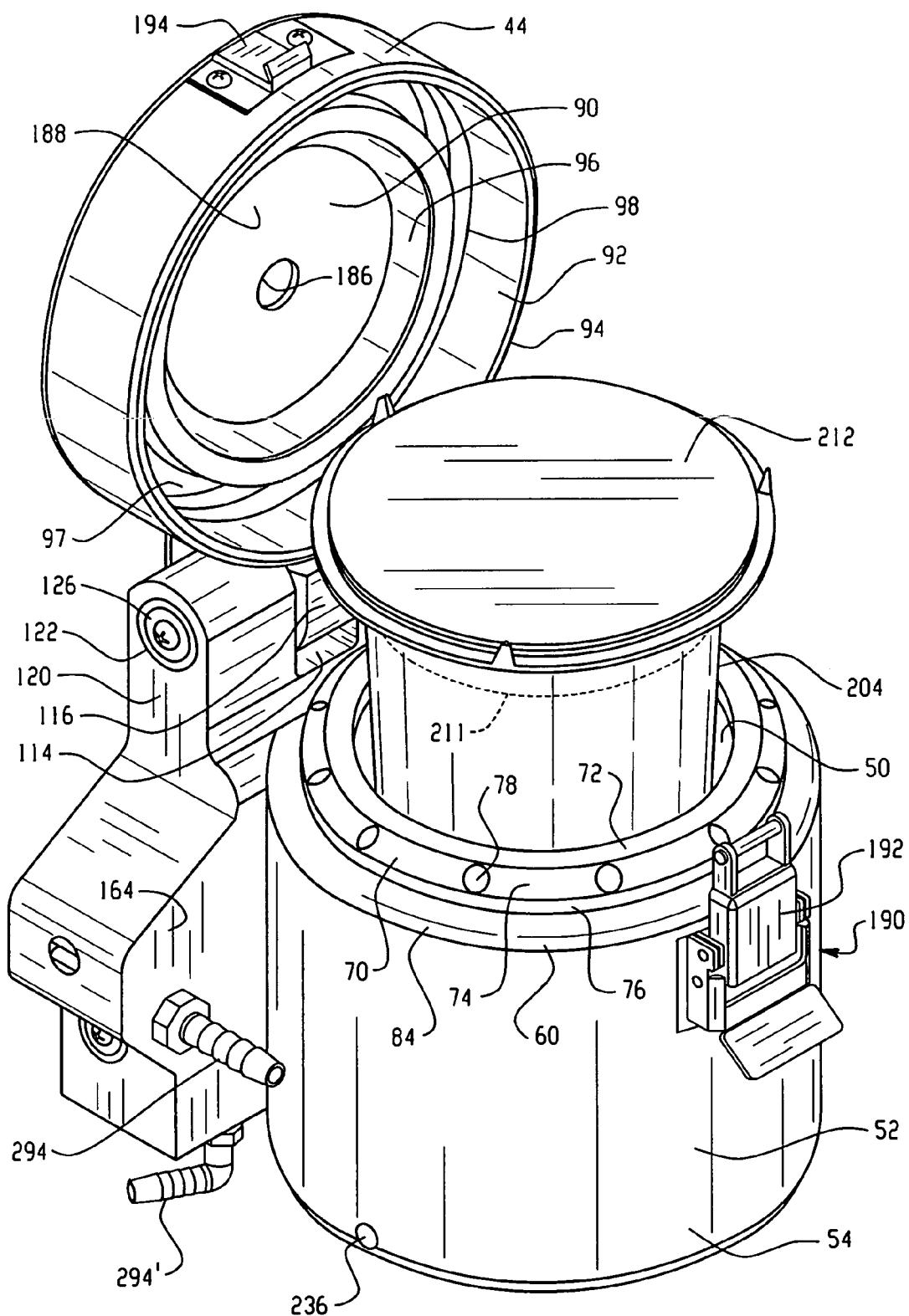
FIG. 6 is an enlarged perspective view of the cartridge holder of FIG. 1, with its lid opened showing the cartridge being positioned in a base of the cartridge holder.

With particular reference to FIGS. 4-6, the base 42 of cartridge holder 30 defines an interior chamber or well 50 for receiving the cartridge 40. In the illustrated embodiment, the base has a cylindrical portion 52 including a sidewall 54, which is closed at a lower end 55 thereof by a base portion 56 and has an opening 58 at an upper end 60 thereof. The cylindrical sidewall 54 has an interior surface 62 which, together with an upper surface 64 of the base portion 56, defines the well 50. The lid 44 of the cartridge holder selectively closes the opening 58 to close the well 50.

With particular reference to FIG. 6, an annular rim 70 extends upward from the upper end 60 of the cylindrical side wall 54 and defines an upper, horizontal annular surface 72, which extends radially inward of the interior surface 62 of the side wall 54. A sloping surface 74 extends downward and radially outward of the upper surface 72 and connects with a vertical side surface 76 of the rim. A plurality of radially spaced apertures 78 (twelve in the illustrated embodiment) are defined in the sloping surface and are connected with the well by corresponding bores 80, which extend at an angle through the rim 70 (FIG. 5). The vertical surface 76 of the annular rim 70 connects with the upper end 60 of the cylindrical portion, radially inward of an outer surface 82 of the cylindrical portion 52, to define an annular peripheral shelf 84, which slopes downwardly and radially outwardly of the vertical surface 76. The annular rim 70 and cylindrical portion 52 of the cartridge holder base 42 may be separately formed and welded together, adhesively attached, threadably connected, or otherwise attached together. Alternatively, the rim 70 and cylindrical portion 52 are integrally formed, for example by molding, with the bores 80 formed during the molding process or subsequently thereto.

With continued reference to FIGS. 4-6, the lid 44 includes a top 90 and an annular peripheral skirt 92, which depends from a peripheral edge of the top. The annular skirt 92 defines a lower surface 94 at a distal end thereof. An annular inner skirt or sealing rim 96 depends from the top and is spaced inward from the annular skirt 92, such that a channel or groove 97 is defined between the peripheral skirt 92 and rim 96. The inner rim 96 defines a lower surface 98 at a distal end thereof. The skirt 92 is slightly longer than the inner rim 96. When the lid 44 is in the closed position, the lower surface 98 of the inner rim 96 is seated or closely adjacent to the upper surface 72 of the annular rim 70 of the base. The lower surface 94 of the skirt 92 is seated above and slightly spaced from the annular peripheral shelf 84 to define an annular space or gap 100 therebetween (FIG. 5), which communicates between the apertures 78 and the exterior of the cartridge, via the groove 97. Liquid is thus able to flow from the well 50 of the cartridge into the reprocessing chamber 12 via the bores 80, groove 97, and gap 100, even when the lid 44 is closed.

With reference once more to FIG. 3, the lid 44 is connected with the mounting member 46 by a hinge 110. Specifically, an upper end of the mounting member includes a clevis 112 with a U-shaped slot 114, which receives a hinge portion 116 of the cartridge lid 44 therein. The hinge portion 116 is pivotally connected to side members 118 and 120 of the clevis 112 by a hollow pivot pin 122. Specifically, the hinge portion 116 and side members 118, 120 each have a bore therethrough for receiving the pivot pin 122. As shown in FIG. 5, the pin 122 defines an interior chamber 124 and is capped with end caps 126 at either end. The caps lock the pivot pin 122 to the side members 118, 120 and prevent fluid flow from the ends of the interior chamber 124.

With particular reference to FIG. 1, the cartridge holder 30 is fluidly connected with a fluid distribution system 128 of the reprocessor 10. Fresh water enters the fluid distribution system 128 via a water inlet line 130. The water is preferably pretreated to remove impurities, such as water hardness salts, and destroy or remove harmful organisms. For example, the water may be sterilized, distilled, filtered, passed through an ion exchange system and/or subjected to other treatment processes before entering the reprocessor. Alternatively, or additionally, the reprocessor 10 may incorporate its own water treatment equipment, such as a filter 132.

The fluid distribution system 128 includes a pump 140, which pumps the water through a fluid line 142 to a manifold 144. The manifold 144 is connected by fluid lines 146, 148 to upper and lower rotating spray bars 150, 152, mounted at upper and lower ends of the chamber 12, respectively. The spray bars 150, 152 spray the water over the rack and the items to be decontaminated. Alternatively, or additionally, other spray means, such as nozzles (not shown), are mounted to walls of the chamber for delivering the water and disinfectant solution to the chamber 12. The water or disinfectant solution drips off the items in the chamber and collects in a sump 154 at the base of the reprocessor chamber 12. At least a portion of the incoming water is supplied to the cartridge holder 30 to mix with the source of disinfectant and form a disinfectant solution. Specifically, the water is carried from the manifold 144 to the chamber 12 via a fluid line 156.

The fluid line 156 is fluidly connected with an outlet port 158 mounted in the rear wall 38 of the chamber 12. A heater 160 in one of the fluid lines heats the circulating fluid on its way to the spray bars 150, 152 or cartridge holder 30.

With particular reference to FIG. 3, the cartridge holder 30 includes a connector or cartridge inlet port 164, which extends rearwardly from a side portion 166 of the mounting member 46 and passes through a suitably positioned opening in the bracket 32. The connector 164 is tapered to be frictionally received within the outlet port 158 when the rack 14 is pushed rearwardly into the chamber 12. Fluid flowing from the outlet port 158 enters the cartridge holder 30 via the connector 164.

With reference to FIG. 5, the side portion 166 of the mounting member 46 defines an interior fluid passage 170 which is connected at an upstream, first end 172 with the connector 164 and at a downstream, second end 174 with an aperture 176 formed in the hollow pivot pin 122, which provides access to the interior chamber 124 of the pin. The top 90 of the cartridge holder lid 44 defines a second interior fluid passage 178, which is connected at an upstream, first end 180 with a second aperture 182 in the hollow pivot pin and at a downstream, second end 184 with a central opening 186 in a lower surface 188 of the top 90 of the lid.

Fluid flows downstream, from the connector 164, through the cartridge holder 30 along a fluid flow path marked by arrows A (FIG. 5). Specifically, the incoming water flows through the first passage 170 and into the interior chamber 124 of the pivot pin 122 via the first pivot pin aperture 176. The fluid flows from the interior chamber 124 and into the second passage 178 in the lid 90 via the second pivot pin aperture 182. The pump 140 supplies the water at sufficient pressure that it sprays out of the central opening 186 as a jet stream.

With reference to FIGS. 4 and 5, the cartridge 40 is positioned in the base 42 of the cartridge holder 30 prior to the start of a decontamination cycle and the lid 44 is closed. A locking assembly 190, at an opposite end of the cartridge holder from the hinge 110, is used to lock the lid 44 to the base 42 during the decontamination cycle. A suitable locking assembly is an overcenter clamp including an overcenter latch 192, mounted on the base 42, which engages a catch 194, mounted on the peripheral skirt 92 of the lid 44, although other locking members are also contemplated.

Figure 7:
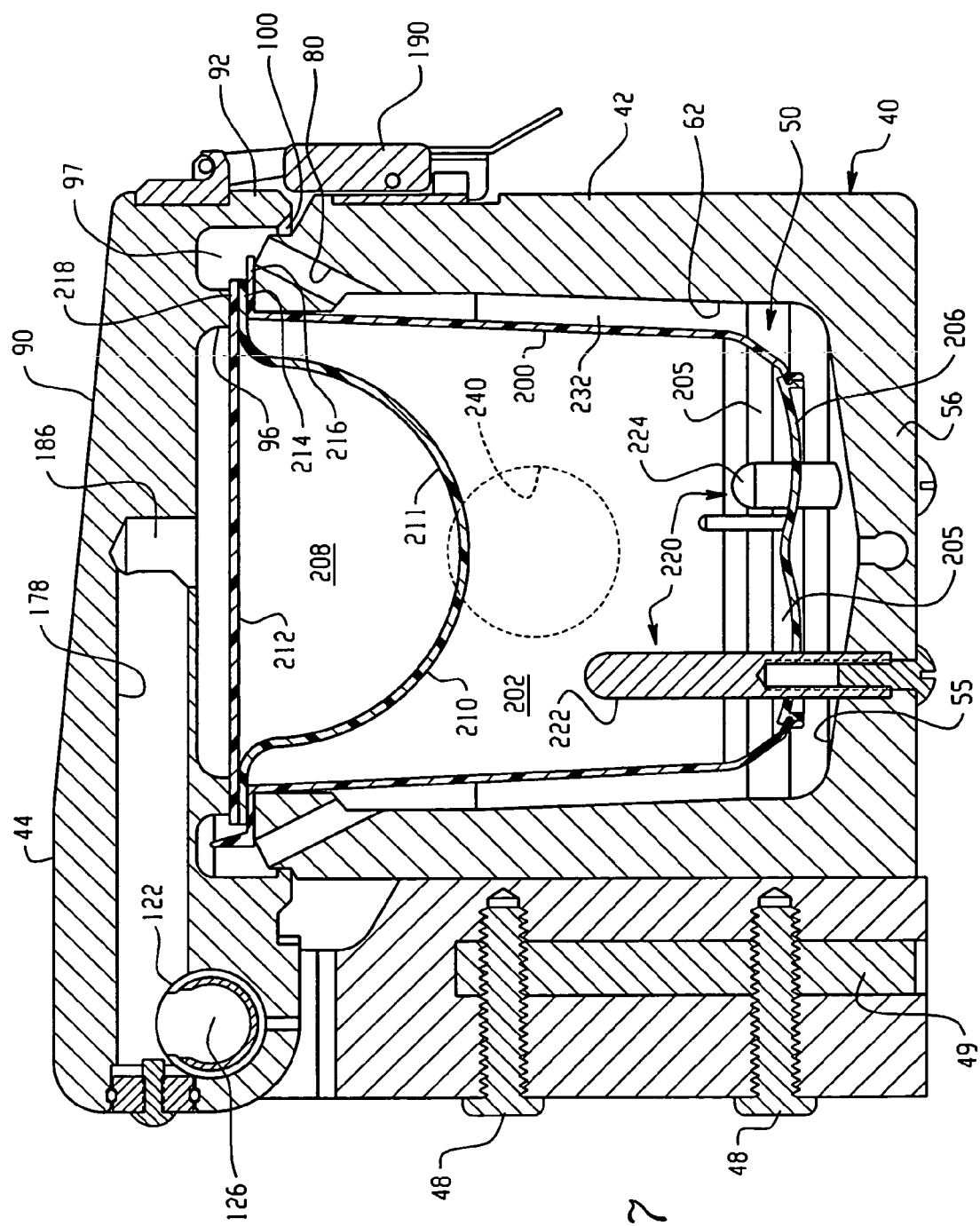
FIG. 7 is an enlarged side sectional view of the cartridge holder of FIG. 1, with its lid in a closed position.

In a preferred embodiment, best shown in FIGS. 5 and 7, the cartridge 40 includes an outer cup portion 200, formed from a lightweight, rigid polymeric material, such as polyethylene, which defines a first interior compartment 202. The outer cup portion 200 includes a generally cylindrical side wall 204 having its lower end 205 closed by a snap fit, removable base portion 206. A second interior compartment 208 is defined in an inner cup portion 210. In the preferred embodiment, the inner cup portion includes a hemispherical peripheral wall 211, which is formed, at least in part, from a porous material. The porous wall 211, or porous portion thereof, is permeable to water and circulating disinfectant solution, but is impermeable to the solid chemical components within the compartments. During assembly of the cartridge 40, a porous lid or top cover 212 is sealed around its periphery together with flanges 214, 216 of the inner and outer cup portions 210, 200, respectively, to create the two compartments 202, 208 and a composite annular cup flange 218. During a decontamination cycle, the flange 218 and rims 70, 96 cooperate to block direct fluid flow from the central aperture 186 to the bores 80, ensuring that all, or substantially all, fluid leaving the well 50 first flows through the cartridge 40. Suitable filter materials for forming the inner cup portion 208 and top cover 212 include polypropylene, polyethylene, nylon, rayon, rigid porous media, such as POREX™ expanded plastic, or other porous plastic, fabric, felt, mesh, and analogous materials.

The first compartment 202 of the cartridge 40 contains a measured dose of a first treatment material, and the second compartment 208 holds a measured dose of a second treatment material. Preferably, the outer cup portion 200 is transparent so that the contents of the cartridge 40 are visible therethrough. Where the inner cup portion 210 is porous, the treatment materials are preferably in solid form, for example, powders or other finely divided solids, which readily disperse and dissolve in the water. For example, the first and second treatment materials are reagents, which react in water to form a disinfectant solution.

In a preferred embodiment, the disinfectant solution includes an oxidant, preferably a peracid, such as peracetic acid. In this embodiment, the first compartment holds a first reagent, such as a peroxy donor. Suitable peroxy donors include perborates, such as sodium metaborate. The second compartment holds a second reagent, such as an acetyl donor. Suitable acetyl donors include acetyl salicylic acid. The two reagents react in water to form the oxidant, peracetic acid in the preferred embodiment. One or other of the compartments may additionally contain other additives. For example, surfactants are preferably included to increase removal of soil and improve penetration of the disinfectant solution into cracks and crevices, sequestering agents are added to combat water hardness, corrosion inhibitors reduce corrosion of the devices and reprocessor components by the disinfectant solution, and buffering agents buffer the disinfectant solution to a suitable pH for optimal disinfection.

In alternative embodiments, the cartridge 40 is configured for holding a single liquid or solid disinfectant concentrate, a liquid reagent separate from a solid reagent, two liquid reagents separately, a liquid or solid cleaning concentrate, cleaning and disinfectant concentrates separately, or a combination cleaning/disinfectant concentrate. The cartridge may thus comprise only a single compartment, or more than two compartments, depending on the nature of the chemical components to be accommodated. Additionally, while the cartridge 40 has been described with reference to a porous inner cup portion 210, it is also contemplated that the inner cup portion may be analogously formed to the outer cup portion, i.e., with a detachable base portion. In yet another alternative embodiment, both the inner and the outer cup portions 200, 210 are porous or have a porous portion through which water and dissolved reagents flow.

With reference to FIG. 5, an opening mechanism 220 opens the cartridge to release the concentrated disinfectant or reagents for forming the disinfectant solution. In the preferred embodiment, the opening mechanism includes one or more projections extending from the cartridge holder base 56. In the illustrated embodiment, a pair of projections 222, 224 dislodge and push up the removable base portion 206 of the cartridge as the holder lid 44 is fastened down. The projections 222, 224 are preferably of unequal heights so that the detached cartridge base portion 206 is held in an angled position, encouraging the flow of fluid from the cartridge. The projections are attached to the base 56 of the cartridge holder by threading threaded ends thereof into suitably positioned threaded bores in the base 56.

In an alternative embodiment, the opening mechanism is one which perforates or cuts a hole in the base portion 206 of the cartridge and may be driven upwardly into the well by an actuating member (not shown), such as a ram.

In the embodiment in which the base portion of the cartridge is formed from a porous material, which allows the water and solutions to pass through, the opening mechanism is eliminated.

The water dissolves the reagents or other chemical components within the cartridge 40 as it passes through, thereby forming the disinfectant solution. The disinfectant solution flows out of the cartridge via an opening 230 (FIG. 5) in the cartridge created by removal or otherwise opening of the cartridge base portion 206. The majority of the solution travels upward, in an annular, generally vertically extending space 232 defined between the sidewall 204 of the outer cup portion and the interior, generally vertical surface 62 of the well. The solution flows through the bores 80 and out of the cartridge holder 30 via the gap 100 between the base 42 and lid 44. The solution thus disinfects all of the surfaces of the well 50 during a microbial decontamination cycle.

As best shown in FIG. 5, a small aperture 236 is defined in the base 42 of the cartridge holder 30 at a lowermost portion of the well 50. The aperture 236 allows solution to drain slowly from the well 50 into the reprocessor chamber 12, and ensures that standing water or solution is not left in the well at the end of the cycle.

In an alternative embodiment, the aperture 236 is wider and provides the only outlet for the disinfectant solution from the cartridge holder. In this embodiment, the bores 80 and the gap 100 are eliminated.

A window 240 (FIG. 5) is formed in the cylindrical sidewall 54 of the cartridge holder base 42. The window 240 is sealed by a transparent material, such as glass or plastic. This allows an operator to determine, simply by looking through the window 240, whether a cartridge 40 is positioned in the well 50 and whether the cartridge contains powder or other disinfectant concentrate. This reduces the chance that an operator will accidentally open a cartridge holder 30 in which a fresh cartridge 40 has already been installed and come into contact with the contents of the opened cartridge.

For decontamination cycles where the items are heavily contaminated with bioload, such as blood or other body fluids, the items are optionally cleaned with a cleaning solution, such as a detergent solution or enzymatic cleaner, prior to or during the disinfection step. As shown in FIG. 1, a multi-dose dispenser 250 is optionally mounted within the reprocessor 10 for selectively releasing a measured dose of a concentrated cleaner into the circulating fluids. At the start of the cycle, incoming water mixes with the cleaner concentrate to form the cleaning solution, which is delivered to the spray bars 150, 152 by the pump 140. During this cleaning step, a valve 252 in the inlet line 156 to the cartridge holder 30 is optionally closed, to inhibit the formation and delivery of the disinfectant solution to the reprocessor chamber 12.

Once the cleaning solution has been circulated for sufficient time to remove the bulk of the bioload from the items, a valve 260 in a water outlet line 262 is opened to allow the dirty cleaning solution to pass from the fluid distribution system 128 to a drain. The water outlet line is shown as being connected to the sump 154, although it may be located elsewhere in the fluid distribution system 128. Additional water is then brought into the reprocessor 10 via the water inlet line 130 and the cartridge holder valve 252 is opened to allow the water to mix with the chemical components in the cartridge 40.

Optionally, a detector for detecting whether the disinfectant concentration is effective for disinfection is mounted within or is fluidly connected with the reprocessor chamber 10. The detector may be a chemical indicator 264 (FIG. 1), such as a strip of paper printed with an ink which changes color on exposure to an appropriate concentration of an oxidizing agent for a period of time judged to be sufficient to effect disinfection or sterilization of the items within the reprocessor. Or, the detector may be a biological indicator which contains a population of microorganisms which show resistance to the decontamination process. In another embodiment, a peracetic acid sensor system is mounted within or is fluidly connected with the reprocessor chamber 10 to provide for continuous monitoring of the peracetic acid concentration.

Figure 8:
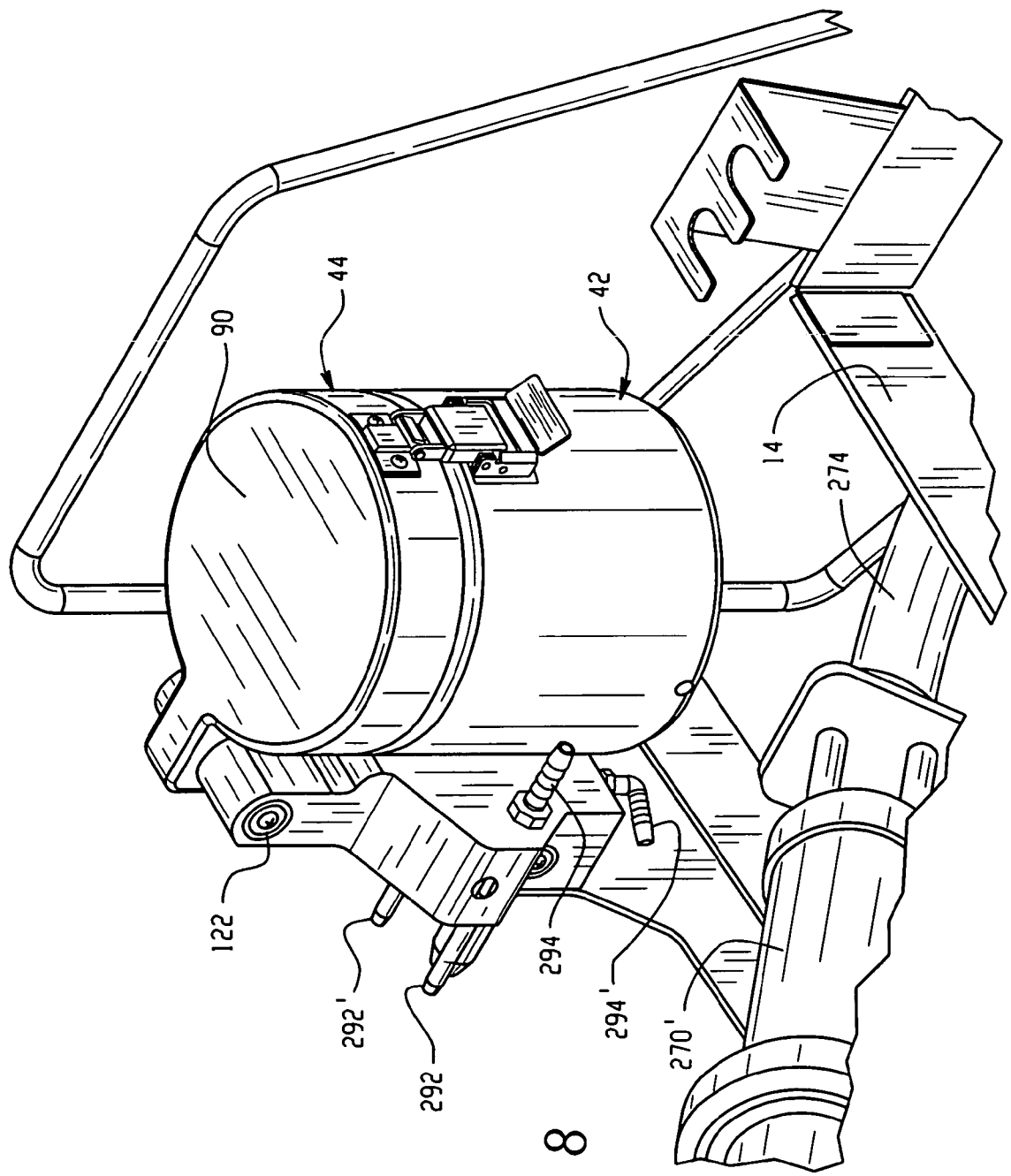
FIG. 8 is an enlarged side perspective view of the cartridge holder of FIG. 1, with its lid in a closed position and the endoscope head container open to receive an endoscope.

With reference once more to FIGS. 1 and 2, and reference also to FIG. 8, the rack 14 is adapted to accommodate two endoscope head receiving containers 270, 270', generally positioned at right angles to one another, although it is contemplated that fewer or more containers 270, 270' may be accommodated. The containers 270, 270' each define an interior chamber (not shown) into which a head of an endoscope or other lumened device is positioned. Disinfectant solution is supplied to the head containers 270, 270' by fluid lines 272 within the chamber 12. A slight positive pressure is maintained within the head containers 270, 270' so that the fluid is forced through interior lumens of the endoscope. An insertion tube of the endoscope is positioned in a long coiled tube 274, extending from the endoscope head receiving container 270. The tube and endoscope light guide connector cord are positioned on the rack 14.

To ensure that the pressure within the head container 270, 270' is maintained within a preselected range throughout a decontamination cycle (i.e., high enough to ensure lumen flow but not so high as to cause damage), a pressure sensor, such as a pressure transducer 280 (FIG. 1), is mounted so as to detect the pressure of the liquid within the endoscope head container 270, 270'. For example, the pressure transducer 280 is mounted outside the reprocessor chamber 12 and detects pressure within each endoscope head receiving container 270, 270' via an interconnecting tube 282 (FIG. 1). The interconnecting tubes 282 for each container 270, 270' are connected with a respective port 284 on the rear wall of the chamber.

With reference to FIGS. 1 and 3, the mounting member 46 of the cartridge holder 30 advantageously acts as a manifold for making other fluid connections within the chamber 12 in addition to the water connection to the cartridge holder described above. For example, the mounting member 46 is used to interconnect pressure tubes 290, within the chamber, with the connection ports 284. Each tube 290 is connected at one end to the interior chamber of one of the endoscope head containers 270, 270'. Bores (not shown) within the mounting member 46 each fluidly connect a first pressure connector 292, 292', which is selectively interconnected with the respective connection port 284, with one of the tubes 290 via a second pressure connector 294, 294', respectively. Like the connector 164, the pressure connectors 292, 292' frictionally engage and make a leak-tight or at least a substantially leak-tight connection with the respective port 284 when the rack 14 is pushed back into the chamber 12 prior to the start of a microbial decontamination cycle. This reduces the number of connections an operator has to make and ensures that one of the connections is not accidentally overlooked.

With reference to FIG. 1, the pressure transducer 280 is connected with a control system 296 which monitors the detected pressures and accesses an algorithm, look-up table, or the like. If the pressure detected falls below a minimum preselected pressure or rises above a maximum preselected pressure, the control system 296 makes a response. The response may be to actuate an alarm, such as a siren or flashing light (not shown), which indicates to an operator that the pressure is outside the desired range. Or, the control system 296 may abort the cycle. In yet another embodiment, the control system 296 controls the pump 140 to increase or decrease the pressure of liquid until the pressure within the housing is in the preselected range. In yet another embodiment, the control system 296 controls a controllable restrictor or valve 298 in the inlet line 272, such as a solenoid valve, to limit or increase the volume of liquid entering the endoscope head container 270, 270' in accordance with the detected pressure.

Operation of the reprocessor 10 typically proceeds as follows: A fresh single use cartridge 40 is placed in the well 50 of the cartridge holder 30 and the lid 44 of the cartridge holder is closed. If the operator finds the cartridge holder lid 44 is closed, a look through the window 240 confirms whether the cartridge holder 30 is empty. The overcenter clamp 190 is operated to clamp the lid 44 to the base 42, clamping the flange 218 of the cartridge between the upper and lower annular rim surfaces 98, 72. Items to be disinfected are placed on the cart 14. During loading, the cart 14 is supported by the opened door 20. The head of an endoscope to be cleaned is positioned in one of the head containers 270, 270'. The cart 14 is wheeled into the reprocessor chamber engaging the connectors 164, 292, 292' with their respective ports 158, 284. The door 20 is closed. A valve 300 in the water inlet line 130 is opened and water enters the fluid distribution system 128. Once sufficient water for a decontamination step has been admitted, the valve 300 is closed. The water is heated to a suitable temperature for decontamination, preferably 45-55° C. in the case of peracetic acid. Water enters the cartridge holder 30 and flows through the porous top 212 of the cartridge. The water mixes with the reagent in the upper compartment 208. The water and dissolved second reagent passes through the porous second cup portion wall 211 and enters the lower compartment 202, where the first reagent dissolves and reacts with the dissolved second reagent to form the disinfectant solution. The disinfectant solution flows out of the cartridge holder 30 and into the reprocessing chamber 12.

The pump 140 recirculates the solution from the sump 154 through the spray bars 150, 152, the head containers 270, 270', and the cartridge holder 30, as discussed above. After the disinfectant solution has been circulated for a sufficient time to disinfect the exterior and interior surfaces of the endoscopes and to disinfect other items in the reprocessor, the drain valve 260 in the sump 154 is opened once more and the disinfectant solution allowed to flow into the drain line 262. Fresh water is then introduced to the reprocessor 10 via the inlet line 130, or via a separate line (not shown), which is connected with a supply of highly purified water, to rinse the endoscope and other items. The water for this step is preferably purified, to reduce the chance for recontamination. For example, heat sterilized, micro-filtered, distilled, deionized, or other purified water is used for the rinse step. Optionally, the rinse water is mixed with a volatile agent, such as alcohol, to promote water removal. Finally, an air drying cycle is employed. With reference to FIG. 1, fresh air is directed by a fan 310 into the head containers 270, 270' and optionally also into the chamber 12. Preferably, the entering air or other drying gas is passed through a filter 312, such as a HEPA filter, to remove unwanted particles and microorganisms. The air may be heated to speed drying, although not above a temperature which could cause damage to the endoscope or other devices being disinfected.

Other steps are optionally included in the cycle, or one or more of the steps eliminated or combined. For example, separate cleaning and disinfection steps may be performed, for example, by including separate compartments in the cartridge which are selectively opened to release first the cleaner concentrate and, subsequently, the disinfectant concentrate. Alternatively, the cleaner concentrate is contained elsewhere in the reprocessor 10, as discussed above. One or more leak testing steps are optionally included. For example, the endoscope is leak tested prior to being placed in the head container 270, 270' to ensure that the lumens which are intended to be leak tight do not permit water to enter and cause damage to sensitive components during reprocessing. Alternatively, a leak testing step may be carried out after positioning the endoscope in the container 270, 270', either before or after inserting the container into the reprocessor chamber. A further leak test may be carried out after reprocessing to ensure that the endoscope has not been damaged during reprocessing.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A decontamination system comprising:
   a chamber for receiving an item to be decontaminated;
   a cartridge holder, mounted within the chamber, which receives a single use cartridge containing a concentrated decontaminant or reagents which mix with water to form a decontaminant solution, the cartridge holder including:
     a base which defines a well having an opening through which the cartridge is inserted into the well,
     a lid which selectively closes the well opening, and
     a plurality of bores adjacent an upper end of the well which fluidly communicate between the well and the chamber, such that water entering the well is directed first through the cartridge before exiting the well through the bores; and
   a fluid distribution system, fluidly connected with the cartridge holder for supplying the water to the well.

2. The decontamination system of claim 1, wherein the base and lid define a gap therebetween, radially outward of the opening, the bores fluidly communicating with the gap.

3. The decontamination system of claim 1, wherein the lid includes an annular rim and the base includes an annular rim, the annular rims clamping a flange at an upper end of the cartridge therebetween when the lid is closed.

4. The decontamination system of claim 3, wherein the lid includes an annular skirt, radially outwardly spaced from the annular rim, the annular skirt being spaced from an upper surface of the base to define a gap therebetween when the lid is closed.

5. The decontamination system of claim 1, further including a locking assembly which selectively locks the lid to the base.

6. The decontamination system of claim 1, wherein the lid defines a first fluid passage and an aperture which fluidly connects the fluid passage with the well when the lid is closed.

7. The decontamination system of claim 6, wherein the lid is pivotally connected with the base by a hinge and wherein the hinge defines a second fluid passage therethrough which is fluidly connected with the first fluid passage.

8. The decontamination system of claim 6, further including a fluid connector, mounted to the cartridge holder, the connector being configured for selectively interconnecting the second fluid pathway with a fluid port of the fluid distribution system.

9. The decontamination system of claim 1, further including a rack for supporting the items, the rack being movable between a first position, in which items are loaded onto the rack, and a second position, in which the rack is positioned within the chamber, the cartridge holder being carried by the rack.

10. The decontamination system of claim 9, wherein the cartridge holder includes a connector fluidly connected with the well by a passageway in the cartridge holder, the connector being selectively connectable with a fluid port of the fluid distribution system when the rack is moved to the second position.

11. The decontamination system of claim 10, wherein the cartridge holder includes a second connector for selective interconnection with a second fluid port, the system further including:
    a container carried by the rack for receiving a portion of the item;
    a fluid line fluidly connecting the container and the connector for fluidly interconnecting the container with the second port when the rack is moved to the second position.

12. The decontamination system of claim 11, wherein the second fluid port is fluidly connected with a pressure detector for detecting the fluid pressure within the container.

13. The decontamination system of claim 1, further including:
    a pump fluidly connected with the fluid distribution system, and
    spray means, mounted within the chamber and fluidly connected with the fluid distribution system, for spraying the decontaminant solution over the item.

14. The decontamination system of claim 1, further including:
    an aperture at a lower end of the base, through which disinfectant solution drains from the well into the chamber.

15. The decontamination system of claim 1, further including:
    a window, defined in the base, through which the cartridge is visible when the lid is closed.

16. A cartridge holder for mounting in a chamber of a decontamination system which receives an item to be decontaminated comprising:
    a base which defines a well for receiving a single use cartridge having a side wall, a water inlet adjacent one end of the side wall, an outlet adjacent another end of the side wall, and a flange extending peripherally from the side wall and containing a concentrated decontaminate or reagents which mix with water to form a decontamination solution, the base having a cartridge receiving opening and a peripheral flange receiving seat for receiving the flange of the cartridge adjacent an upper end thereof, the base including a plurality of bores disposed on a cartridge outlet side of the flange receiving seat which extend from the well to an exterior surface of the base adjacent the opening;

a lid which selectively closes the opening, the lid including a flange engaging seat for engaging the flange of the cartridge;
a fluid passageway at least partially defined by the lid and partially defined by the base, the fluid passageway having an outlet surrounded by the flange engaging seat; and
a connector connected with the fluid passageway for connecting the fluid passageway with a water supply of the decontaminating system to supply water to the well, such that with a cartridge received in the well and the lid closed, water flows through the fluid passage, out the fluid passage, in the cartridge inlet, dissolves the contaminant or reagents, flows out the cartridge outlet, through the well, and out through the bores.

17. A cartridge holder comprising:
a base which defines a well for receiving a cartridge having a side wall, the base having an opening adjacent an upper end thereof, the base including a plurality of bores which extend from the well to an exterior surface of the base adjacent the opening;
a lid which selectively closes the opening;
a hinge which pivotally connects the lid and the base, the hinge including a pivot pin which defines an interior chamber; a fluid passageway defined through an upper wall portion of the base, the interior chamber of the pivot pin and the lid, the fluid passage being fluidly connected with the well; and
a connector mounted to the base in fluid communication with the fluid passage such that water received through the connector passes through the fluid passage in the base upper wall portion, the pin interior passage, and the lid into the well.

18. A method of disinfection comprising:
placing a cartridge in a well defined by a base through an opening in the well, the cartridge having a side wall and upper and lower ends which selectively hold within the cartridge a disinfectant concentrate or reagents which react in a liquid to form a disinfectant solution:
closing the opening in the well with a lid;
supplying the liquid to the well such that:
    the liquid flows into the cartridge through the upper end,
    the liquid mixes with the concentrate or reagents to form the disinfectant solution, and
    the disinfectant solution flows out of the cartridge into the well through the lower end of the cartridge;
flowing the disinfectant solution through a space defined between the cartridge side wall and the well to disinfect the well;
flowing the disinfectant solution out of the well through bores in the base adjacent an upper end of the well.

19. The method of claim 18, further including:
flowing the liquid into the well through a passageway at least partially defined through the lid.

20. The method of claim 19, wherein the lid is pivotally connected to the base by a hinge, and the passageway is at least partially defined in the hinge.

21. The method of claim 18, further including:
draining a portion of the disinfectant solution through a hole at a lower end of the well.

22. The method of claim 18, wherein the well is fluidly connected with a connector, the connector being carried by a movable rack, the method further including:
wheeling the rack into a chamber, the connector automatically connecting with a fluid outlet port within the chamber as the rack is wheeled into the chamber.

23. The method of claim 18, wherein the step of closing the opening includes clamping an annular flange at an upper end of the cartridge between a first surface defined by the lid and a second surface defined by the base, the bores defining openings which are radially outwardly spaced from the first surface, such that substantially all liquid leaving the well passes through the cartridge.

24. The method of claim 18, further including:
contacting items to be disinfected with the disinfectant solution.

25. A disinfection apparatus comprising:
a cartridge received in a well defined by a base through an opening in the well, the cartridge having a side wall and upper and lower ends which selectively hold within the cartridge a disinfectant concentrate or reagents which react in a liquid to form a disinfectant solution;
a lid closing the opening in the well;
a means for supplying the liquid to the well such that:
    the liquid flows into the cartridge through the upper end,
    the liquid mixes with the concentrate or reagents to form the disinfectant solution, and
    the disinfectant solution flows out of the cartridge into the well through the lower end of the cartridge;
    the cartridge side wall and the well defining a space between the cartridge side wall and the well through which the disinfectant solution flows to disinfect the well;
    bores defined in the base adjacent an upper end of the well through which bores the disinfectant solution flows out of the well.

26. A cartridge holder for mounting in a chamber of a decontamination system which receives an item to be decontaminated comprising:
a base which defines a well for receiving a single use cartridge containing a concentrated decontaminate or reagents which mix with water to form a decontamination solution and having a side wall, the base having an opening adjacent an upper end thereof, the base including a plurality of bores which extend from the well to an exterior surface of the base adjacent the opening;
a lid which selectively closes the opening;
a fluid passageway at least partially defined by the lid and partially defined by the base, the fluid passageway being fluidly connected with the well;
a connector connected with the fluid passageway for connecting the fluid passageway with a water supply of the decontaminating system to supply water to the well;
wherein the fluid passageway extends from the connector which receives water from the water supply, through the base without entering the well, from the base to the lid without flowing into the well, through the lid, and from the lid through an outlet opening into the well.

27. A cartridge holder for mounting in a chamber of a decontamination system which receives an item to be decontaminated comprising:
a base which defines a well for receiving a single use cartridge containing a concentrated decontaminate or reagents which mix with water to form a decontamination solution and having a side wall, the base having an opening adjacent an upper end thereof, the base including a plurality of bores which extend from the well to an exterior surface of the base adjacent the opening;
a lid which selectively closes the opening;

a fluid passageway at least partially defined by the lid and partially defined by the base, the fluid passageway being fluidly connected with the well;

a connector connected with the fluid passageway for connecting the fluid passageway with a water supply of the decontaminating system to supply water to the well; and, bores extending through the base from the well to a groove defined between the base and the lid, the base and the lid defining a gap through which fluid from the groove is discharged, fluid flowing through the bores, groove, and gap being isolated from the fluid passage such that fluid flowing through the fluid passage does not intermix with fluid flowing through the bores, the groove, and the gap.

* * * * *